US010814090B2

(12) United States Patent
Jach et al.

(10) Patent No.: US 10,814,090 B2
(45) Date of Patent: Oct. 27, 2020

(54) CARBON DIOXIDE AIRWAY ADAPTOR

(71) Applicant: JADA Medical LLC, Potomac, MD (US)

(72) Inventors: Michael Jach, Bethesda, MD (US); Eduardo Salcedo, Bethesda, MD (US)

(73) Assignee: Jada Medical, LLC, Potomac, MD (US)

( * ) Notice: Subject to any disclaimer, the term of this patent is extended or adjusted under 35 U.S.C. 154(b) by 1464 days.

(21) Appl. No.: 14/827,732

(22) Filed: Aug. 17, 2015

(65) Prior Publication Data
US 2017/0049985 A1    Feb. 23, 2017

(51) Int. Cl.
| | | |
|---|---|---|
| *A61M 16/08* | (2006.01) | |
| *A61M 16/04* | (2006.01) | |
| *A61B 5/091* | (2006.01) | |
| *A61M 16/06* | (2006.01) | |

(52) U.S. Cl.
CPC .......... *A61M 16/085* (2014.02); *A61B 5/091* (2013.01); *A61M 16/0463* (2013.01); *A61M 16/0495* (2014.02); *A61M 16/06* (2013.01); *A61M 16/0672* (2014.02); *A61M 16/0816* (2013.01); *A61M 2202/0208* (2013.01); *A61M 2230/432* (2013.01)

(58) Field of Classification Search
CPC .......... A61M 16/085; A61M 16/0495; A61M 16/0463; A61M 16/06; A61M 16/0672; A61M 16/0816; A61M 2202/0208; A61M 2230/432; A61M 16/04; A61M 16/0488; A61M 16/049; A61M 16/0497; A61M 16/0683; A61M 16/0688; A61M 2209/082; A61M 2209/088; A61M 16/08; A61M 16/0841; A61M 16/0858; A61M 16/0875; A61B 5/091
USPC ..................................................... 128/202.22
See application file for complete search history.

(56) References Cited

U.S. PATENT DOCUMENTS

| | | | | | |
|---|---|---|---|---|---|
| 2,245,658 | A | * | 6/1941 | Erickson | A61M 16/0638 128/206.28 |
| 2,663,297 | A | * | 12/1953 | Turnberg | A61M 16/0666 128/207.13 |
| 2,859,748 | A | * | 11/1958 | Hudson | A61M 16/06 128/206.28 |
| 3,508,543 | A | * | 4/1970 | Aulicono | A61M 16/0048 128/202.28 |
| 3,730,179 | A | * | 5/1973 | Williams | A61M 16/0463 128/204.18 |
| 3,841,319 | A | * | 10/1974 | Michael | A61M 16/0475 601/41 |
| 4,274,406 | A | * | 6/1981 | Bartholomew | A61M 16/0465 128/204.25 |

(Continued)

*Primary Examiner* — Michael J Tsai
(74) *Attorney, Agent, or Firm* — Edell, Shapiro & Finnan, LLC

(57) ABSTRACT

A carbon dioxide airway adaptor can be attached to an oropharyngeal airway device or an oxygen facemask. The adaptor includes a dome-shaped body, an attachment mechanism at the edge of the body to attach the carbon dioxide airway adaptor to the oropharyngeal airway device or oxygen facemask, a port in the body to provide an airway and access for suctioning, a first docking sleeve in the body to provide oxygen supplementation, and a second docking sleeve in the body to provide end-tidal $CO_2$ monitoring.

20 Claims, 16 Drawing Sheets

(56) References Cited

U.S. PATENT DOCUMENTS

| | | | | |
|---|---|---|---|---|
| 4,848,331 A * | 7/1989 | Northway-Meyer | ..................... A61M 16/0488 128/200.26 |
| 5,027,811 A * | 7/1991 | Tuxill | ............... A61M 16/0465 128/207.14 |
| 5,485,837 A * | 1/1996 | Solesbee | ........... A61M 16/0497 128/207.17 |
| 6,857,428 B2 * | 2/2005 | Thornton | ............... A61M 16/06 128/206.21 |
| 7,171,962 B1 * | 2/2007 | Bloem | .................. A61M 16/04 128/200.26 |
| 8,887,729 B2 * | 11/2014 | Harrington | ....... A61M 16/0465 128/207.14 |
| 2003/0094178 A1 * | 5/2003 | McAuley | .......... A61M 16/0666 128/207.18 |
| 2006/0207599 A1 * | 9/2006 | Busch | ............... A61M 16/0816 128/206.24 |
| 2007/0267024 A1 * | 11/2007 | Kremer | ............. A61M 16/0488 128/207.14 |
| 2009/0211574 A1 * | 8/2009 | Sniadach | .......... A61M 16/0488 128/200.26 |
| 2010/0030027 A1 * | 2/2010 | Bastid | ............... A61M 16/0488 600/120 |
| 2012/0048278 A1 * | 3/2012 | Yasick | .................. A61M 16/04 128/207.14 |
| 2012/0138060 A1 * | 6/2012 | Barlow | ............. A61M 16/0688 128/205.25 |
| 2014/0076311 A1 * | 3/2014 | Darab | .................. A61M 16/06 128/203.12 |
| 2015/0265792 A1 * | 9/2015 | Goudra | ............. A61B 1/00154 600/115 |
| 2015/0297852 A1 * | 10/2015 | Ozenne | ............. A61M 16/0493 600/543 |
| 2016/0158476 A1 * | 6/2016 | Tatkov | ............. A61M 16/0688 128/203.22 |
| 2016/0235938 A1 * | 8/2016 | Khabiri | ............... A61M 16/085 |

* cited by examiner

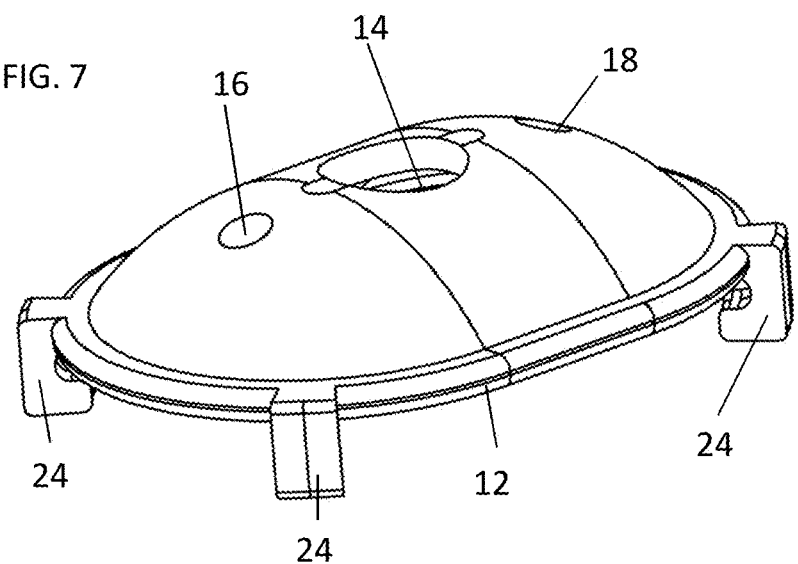
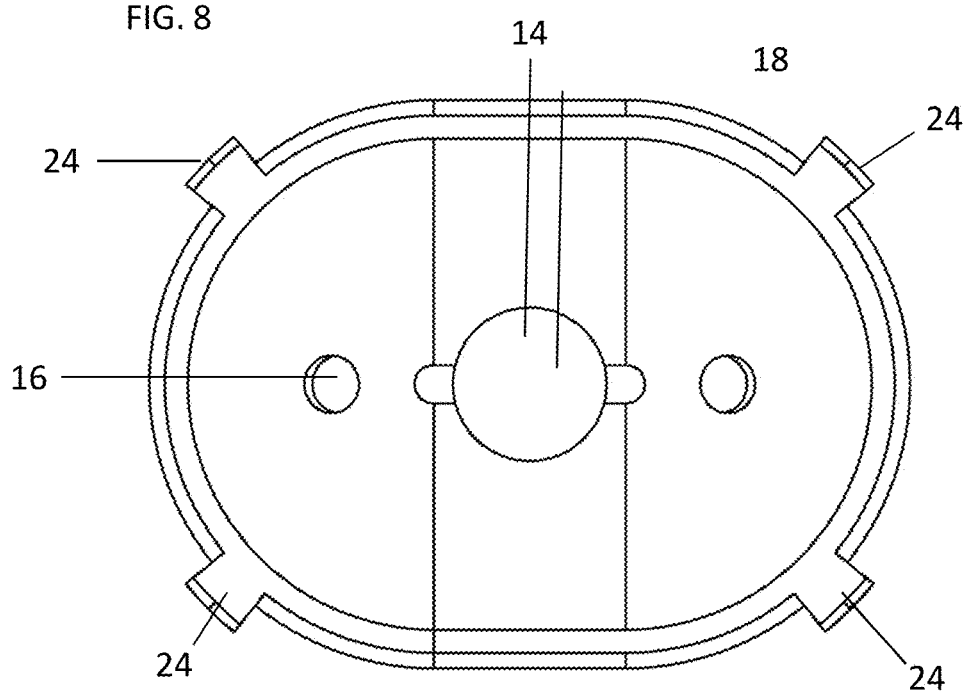

24  24

CARBON DIOXIDE AIRWAY ADAPTOR

TECHNICAL FIELD

The invention relates to medical devices, specifically, the invention relates to medical devices which are able to capture and measure gas exchange from commonly used airway equipment in clinical use.

BACKGROUND

An alternative to general anesthesia is moderate or deep sedation. It differs from general anesthesia in that shorter-acting anesthetics are used and the patient is not put on a ventilator, so that the patient breathes by himself, as if sleeping. Compared to general anesthesia, patients can recover more quickly and experience less postoperative pain, nausea and/or vomiting and a more rapid recovery.

As noted, the patient is required to breathe by himself. In some cases, there may be a concern that the airway is obstructed. For example, the patient may start to snore indicating that the tongue is falling back to block the airway.

A medical device called an oropharyngeal or oral airway device is used to maintain an open airway. It does this by preventing the tongue from covering the epiglottis, which could obstruct airflow. When a person becomes unconscious, the muscles in their jaw relax and allow the tongue to obstruct the airway.

Typically, the oral airway device includes a body with a distal end and a proximal end having a wide and flat flange. Generally, the flange is at an approximate 90 degree angle to the direction of the body. The distal end can be inserted within the pharynx above the epiglottis. The body has a central channel or lumen that allows free flow of air through the device from the distal to the proximal end and also permits suctioning of secretions.

As shown in FIG. 1, the distal end is inserted into the mouth of a patient such that the proximal end of the body is outside and adjacent to the patient's mouth. The flange contacts the entrance of the patient's mouth and serves to prevent the oral airway device from further proceeding into the patient's mouth.

Once the device is properly positioned, the airway is open and the patient can breathe normally. Since supplemental oxygen and monitoring of end-tidal $CO_2$ levels may also be desired, a cannula may be inserted into the oral airway to provide oxygen and another cannula may be inserted into the device to monitor end-tidal $CO_2$ levels. Sometimes these cannulas are taped to the oral airway device.

In a similar fashion, when a oxygen facemask is used, gas exchange can be, measured by using the adaptor over the outflow perforations of the mask.

SUMMARY

The Carbon Dioxide Airway Adaptor (CDAA or adaptor) is designed to provide a means of measuring exhaled carbon dioxide and enhanced oxygen delivery in clinical situations where oropharyngeal airways (OPA) and oxygen facemasks are utilized. It is indicated in a wide variety of clinical circumstances where partial or complete airway obstruction in encountered in the daily practice of anesthesia.

The CDAA provides the clinician with a means of capturing exhaled carbon dioxide at a wide variety of fresh gas flows and provide meaningful data by way of end tidal carbon dioxide tracings while maintaining airway patency with an oropharyngeal airway. It also provides a means of providing supplemental inspired oxygen with a fraction of inspired oxygen ($FiO_2$) superior to that of nasal cannula while maintaining airway patency with an oropharyngeal airway.

The adaptor provides another level of safety to existing airways or oxygen facemasks and complies with efforts to monitor carbon dioxide exchange wherever clinically possible. The ability to monitor end tidal carbon dioxide from an airway or oxygen facemask is also less invasive than a laryngeal mask airway while providing enhanced oxygen delivery. It likely provides more reliable carbon dioxide capture than nasal cannula at commonly used fresh gas flows.

It has the potential to free up the anesthesia provider from maintaining constant chin lift maneuvers in the event of partial or complete airway obstruction and monitoring end tidal carbon dioxide tracings.

Universal adaptors are provided for a wide range of oropharyngeal airways or oxygen facemasks in current clinical use.

The potential clinical scenarios for use include patients receiving regional anesthesia as the primary anesthetic who may obstruct easily at light levels of intravenous sedation. It can also be used for patients receiving TIVA total intravenous anesthesia as an adjunct to local anesthetic field block and develop airway obstruction. The airway adaptor could prevent the need for laryngeal mask airway rescue in many circumstances.

The CDAA may be used for post extubation scenarios where anesthetic depth still mandates an airway with the need for ongoing carbon dioxide monitoring and oxygen supplementation. The airway adaptor can also be used preemptively where airway obstruction is anticipated and the procedure does not require the depth of anesthesia necessary for a laryngeal mask airway or an endotracheal tube. This is seen in many situations where Propofol infusions are used in low to midrange infusion rates. There may be potential usage in intensive care, emergency and other critical care scenarios where oropharyngeal airways or oxygen facemasks are routinely used.

In one general aspect, an oropharyngeal adaptor that attaches to an oropharyngeal airway device includes a dome-shaped body, an attachment mechanism at the edge of the body to attach the oropharyngeal adaptor to the oropharyngeal airway device, a port in the body to provide an airway and access for suctioning, a first docking sleeve in the body to provide oxygen supplementation, and a second docking sleeve in the body to provide end-tidal $CO_2$ monitoring.

Embodiments may include one or more of the following features. For example, the attachment mechanism may be a pair of clips or four clips or brackets.

The attachment mechanism may also be a rail around a portion of the body or a continuous ridge around the body. A collar may be attached to the ridge to fix an oral airway device between the collar and the ridge.

As another feature, a ring with an adhesive on front and back surfaces may be attached to the ridge and an oral airway device or an oxygen facemask.

In another general aspect, an oropharyngeal adaptor that attaches to an oropharyngeal airway device includes a dome-shaped body, a flat ridge at the edge of the body to attach the oropharyngeal adaptor to the oropharyngeal airway device, a first port in the body to provide an airway and access for suctioning, a second port in the body to provide oxygen supplementation, and a third port in the body to provide end-tidal $CO_2$ monitoring.

Embodiments may include one or more of the above or following features. For example, a collar with clips or brackets may be used to fix an oral airway device is between the ridge and the collar. The collar may have slots to receive the clips and fix onto the ridge and the collar together.

A rail with slots may extend from a portion of the ridge and a collar with clips may be used to fix the oral airway device between the ridge and the rail. In this embodiment, the clips may pass through the slots and lock into place.

BRIEF DESCRIPTION OF THE DRAWINGS

FIGS. 7-9 illustrate a second embodiment of the adaptor.

DESCRIPTION OF THE INVENTION

Figure 1:
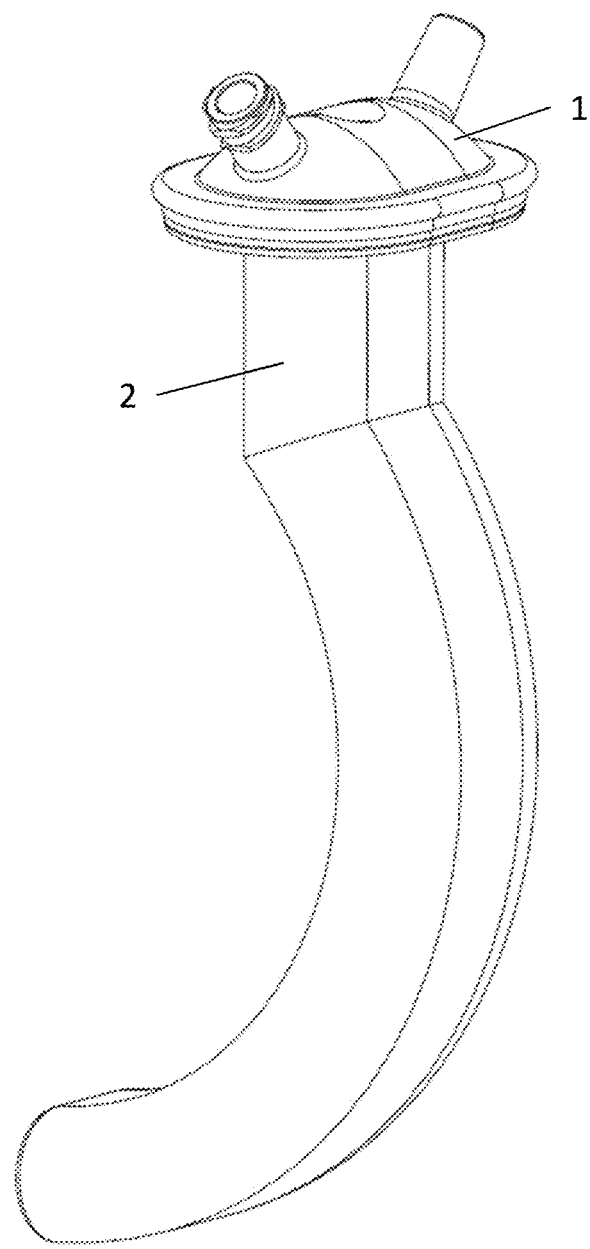
FIG. 1—illustrates an adaptor attached to an oral airway device.

A Carbon Dioxide Airway Adaptor (CDAA or adaptor) facilitates an airway through an oral airway device while providing for oxygen supplementation and end-tidal $CO_2$ level monitoring. As shown in FIG. 1, the adaptor 1 can be attached to the oral airway device 2.

Figure 2:
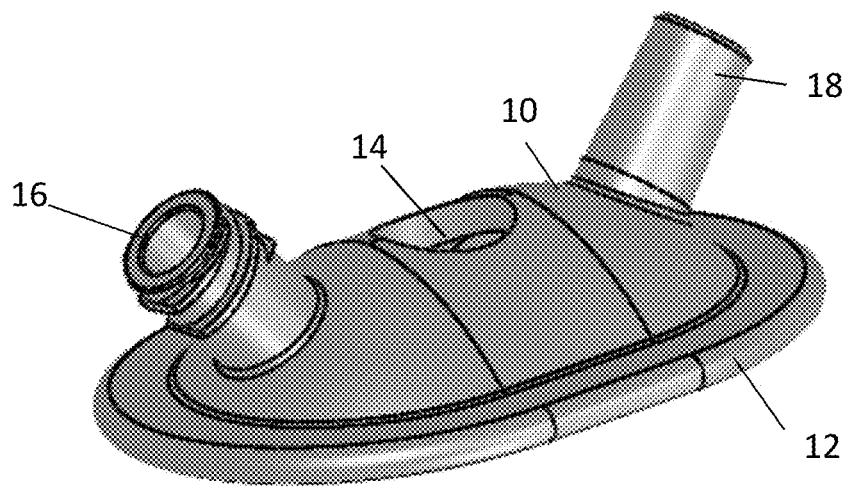
FIGS. 2-6 illustrate a first embodiment of the adaptor.
Figure 3:
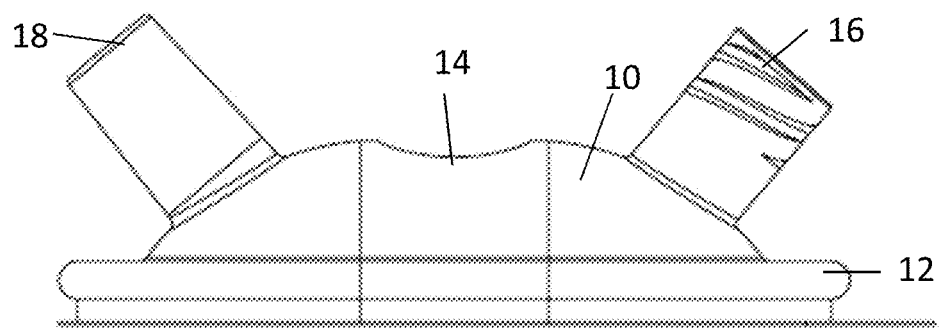
Figure 4:
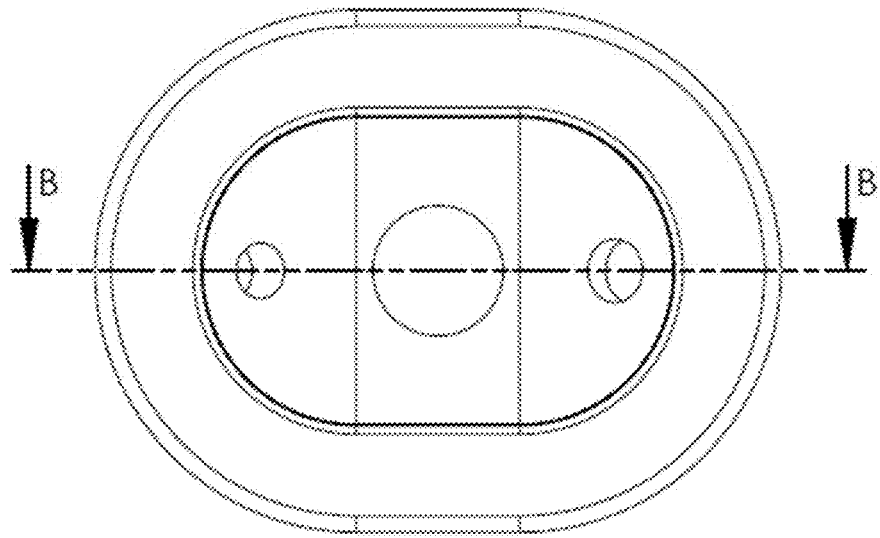

Referring to FIGS. 2-4, the adaptor includes a dome-shaped body 10 surrounded by a wide, flat ridge 12 to attach the adaptor to an oropharyngeal airway device. In the center of the dome-shaped body 10, there is a port 14 to allow free flow of air through the device and to accommodate endoscopic instruments and access for suctioning. A first docking channel 16 and a second docking channel 18 are located adjacent to the central port 14 on the dome-shaped body 10. The first docking channel 16 facilitates attachment of an oxygen line if the patient needs oxygen supplementation, while the second docking channel 18 facilitates attachment of a line connected to an end-tidal $CO_2$ monitor.

Figure 5:
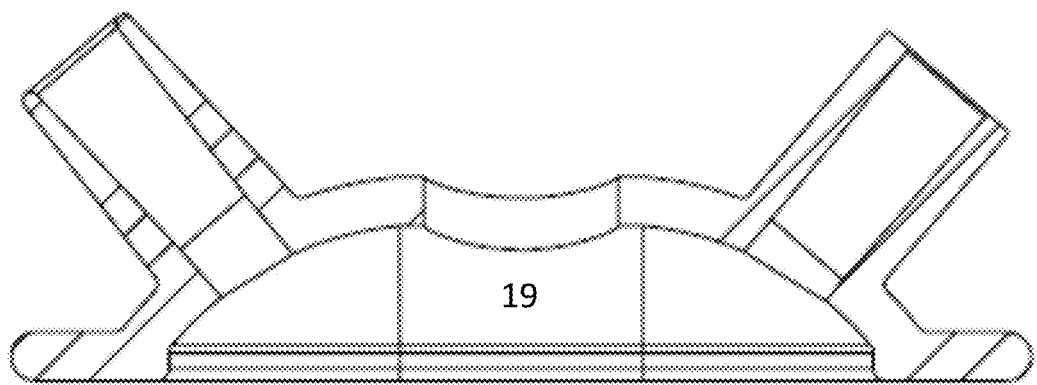

FIG. 5 shows a cut-away view of the adaptor at the line B-B shown in FIG. 4. The cut-away view shows a cavity or chamber 19 with a volume.

Figure 6:
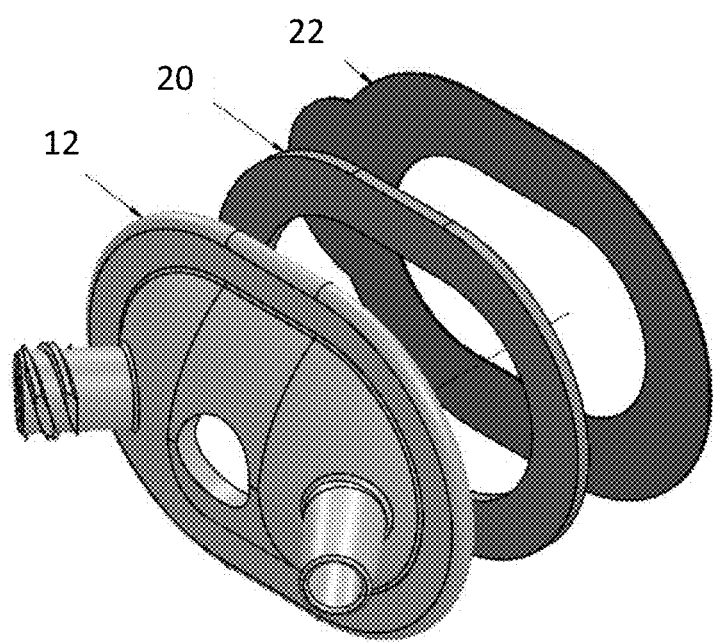

Referring to FIG. 6, the underside of the ridge 12 contains a double-sided adhesive pad 20 with a removable cover 22. The cover 22 must be peeled off the adhesive pad 20 to expose the adhesive side of the adaptor and effectively secure the adaptor onto the oropharyngeal airway or oxygen facemask device and the ridge 12 of the adaptor 1.

Figure 9:
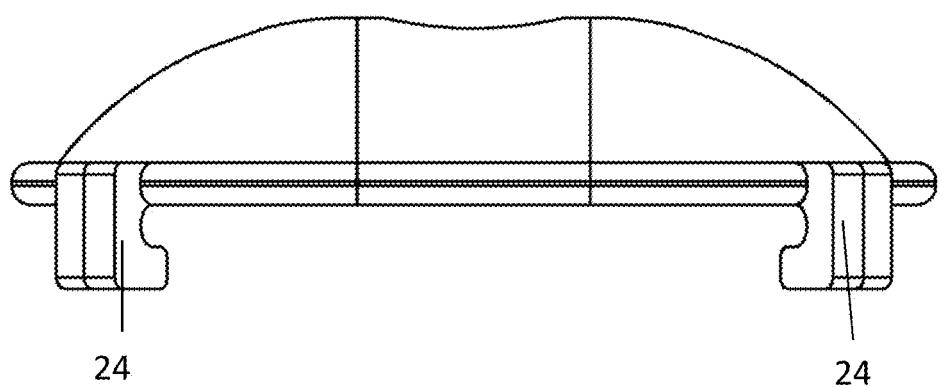

In another embodiment shown in FIGS. 7-9, the adaptor 1 includes a round or dome-shaped body 10 with four clips or brackets 24 extending from the ridge 12 to attach the adaptor to the oral airway device (not shown). The adaptor includes a breathing port 14 and two docking ports 16, 18. One of the docking ports can be attached to an oxygen line or cannula and the other port 18 can be attached to a cannula that attaches to an end-tidal $CO_2$ monitor.

Figure 10:
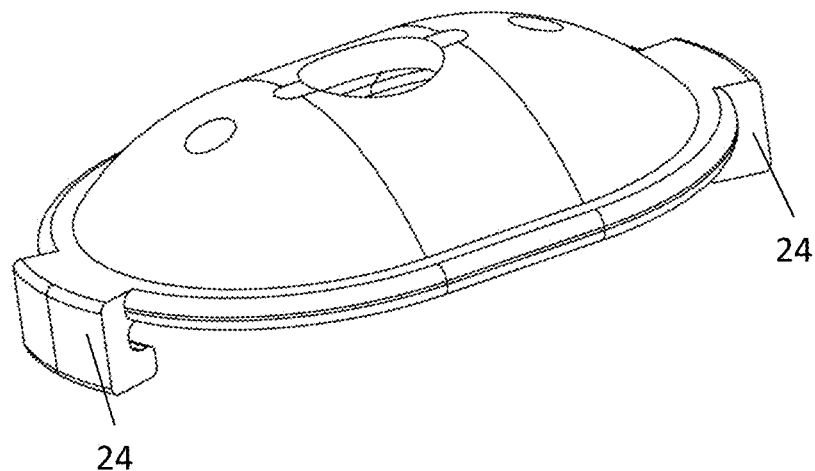
FIGS. 10-12 illustrate a third embodiment of the adaptor.
Figure 11:
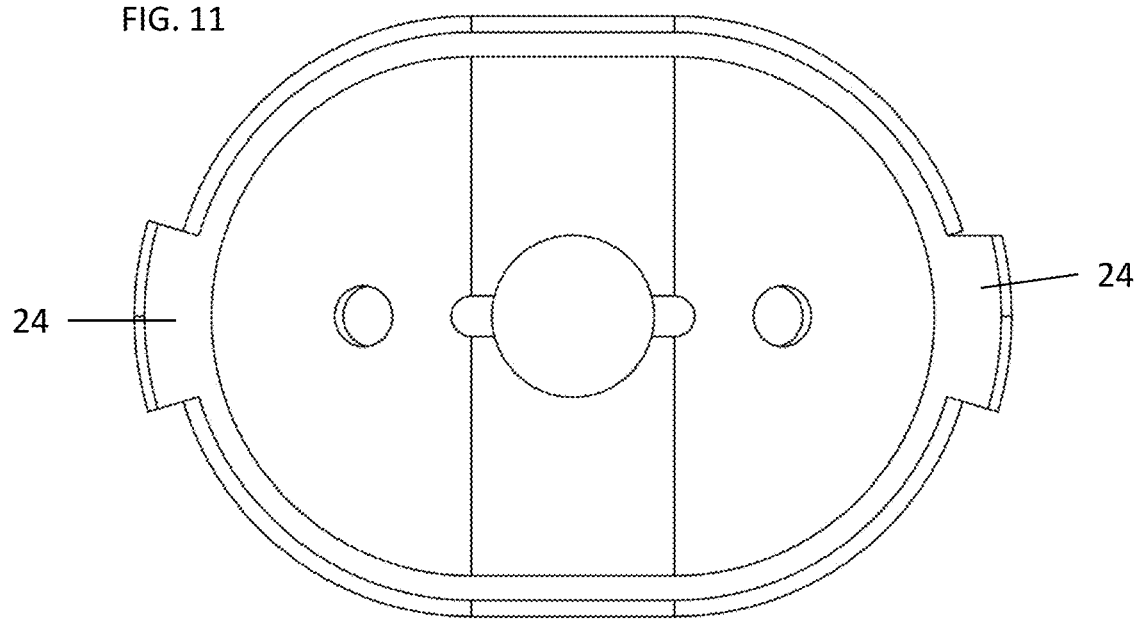
Figure 12:
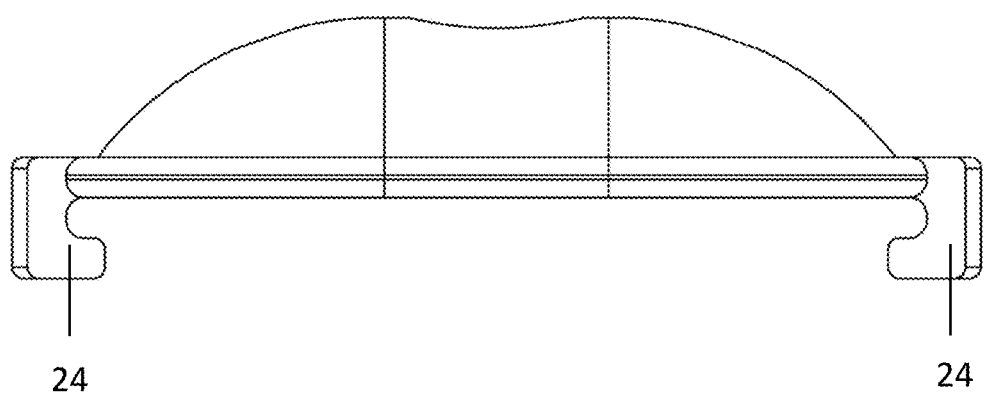

In another embodiment shown in FIGS. 10-12, there is a pair of brackets 24 that attach the adaptor 1 to the oral airway device (not shown).

Figure 13:
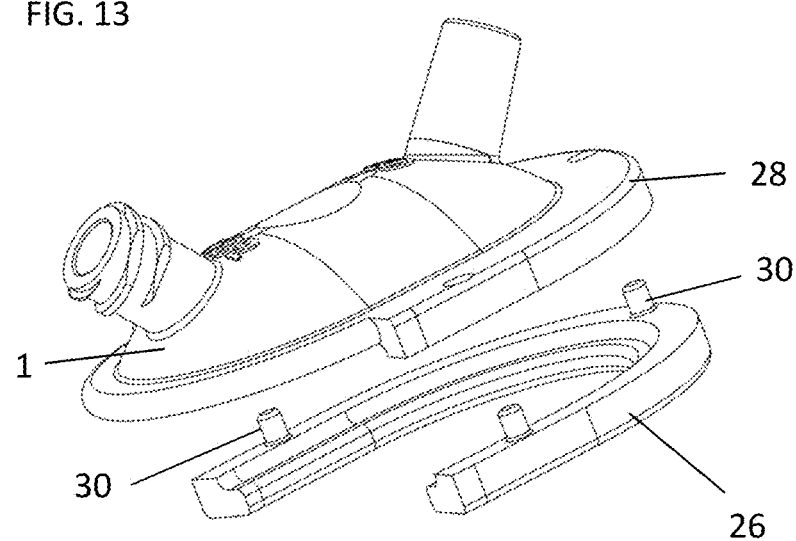
FIGS. 13-15 illustrate a fourth embodiment of the adaptor.
Figure 14:
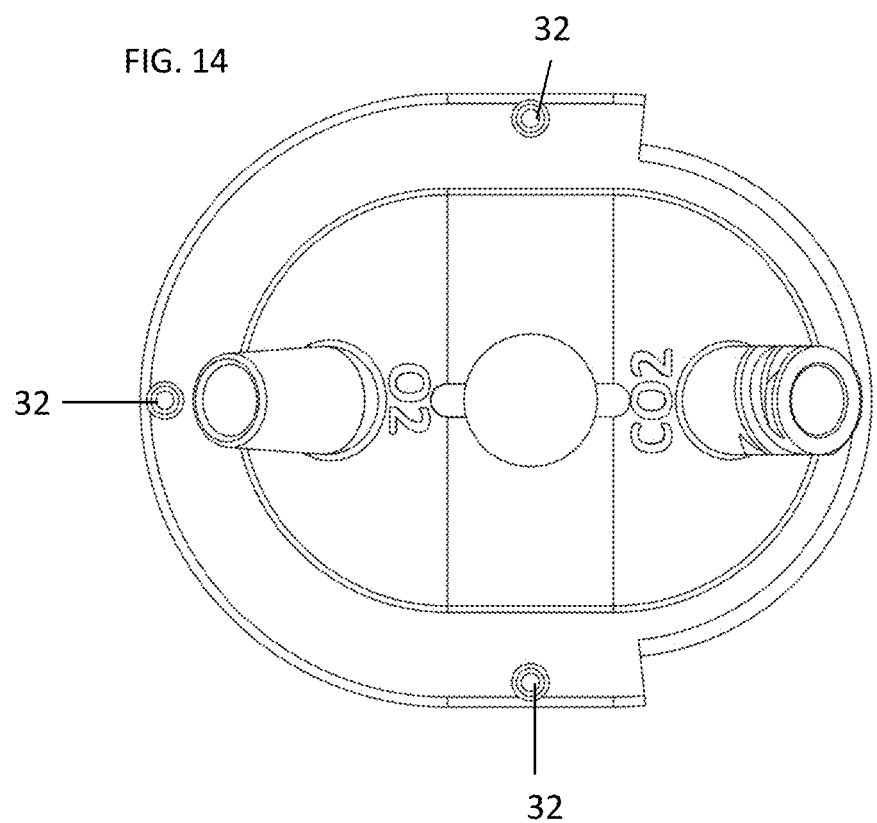
Figure 15:
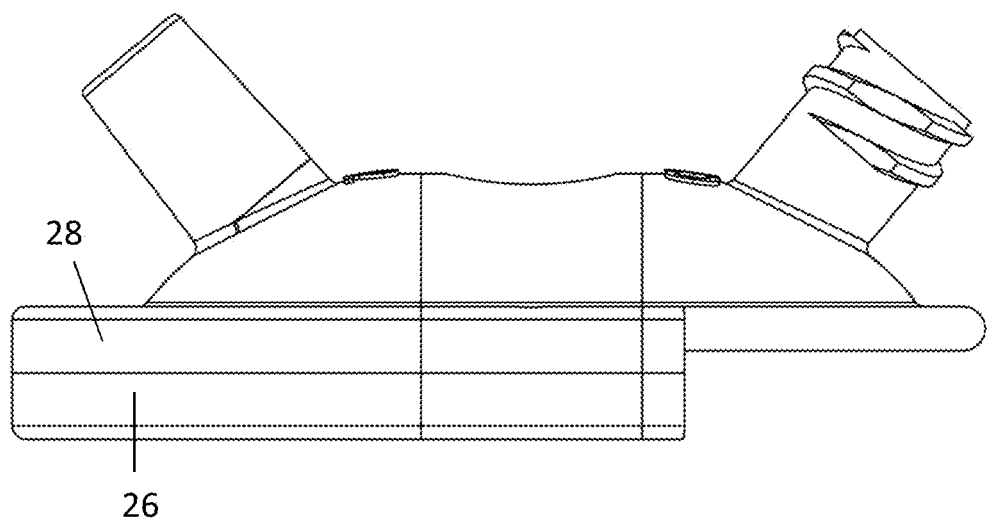

FIGS. 13-15 show another embodiment of the adaptor 1. A collar 26 is attached to the adaptor 1 to secure the adaptor 1 to the oral airway device by sandwiching the device between a partial extended rail 28 on the adaptor and the collar 26. As set of pegs 30 on the collar 26 fits into three receiving holes 32.

Figure 16:
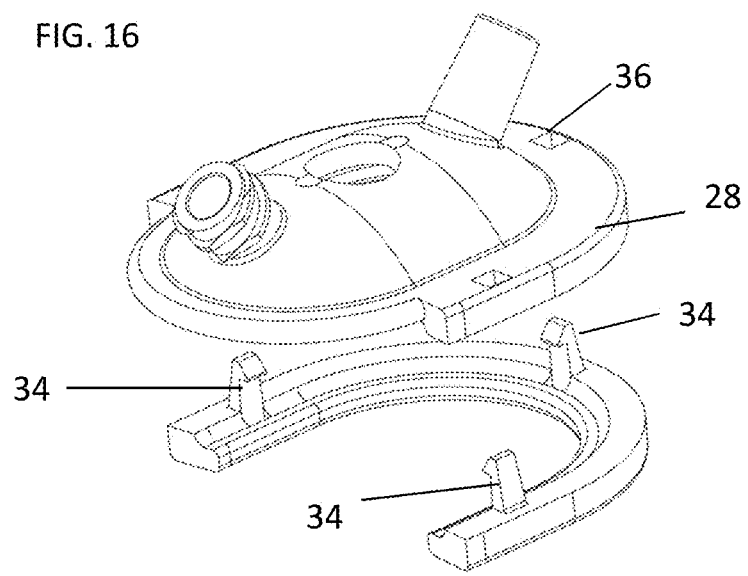
FIGS. 16-18 illustrate a fifth embodiment of the adaptor.
Figure 17:
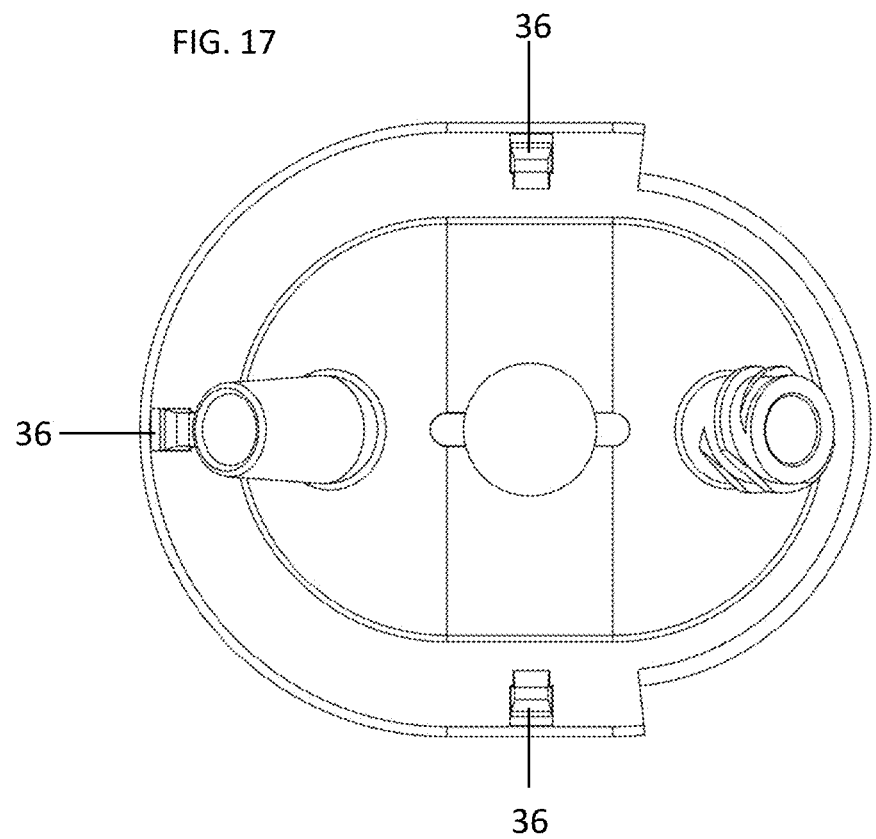
Figure 18:
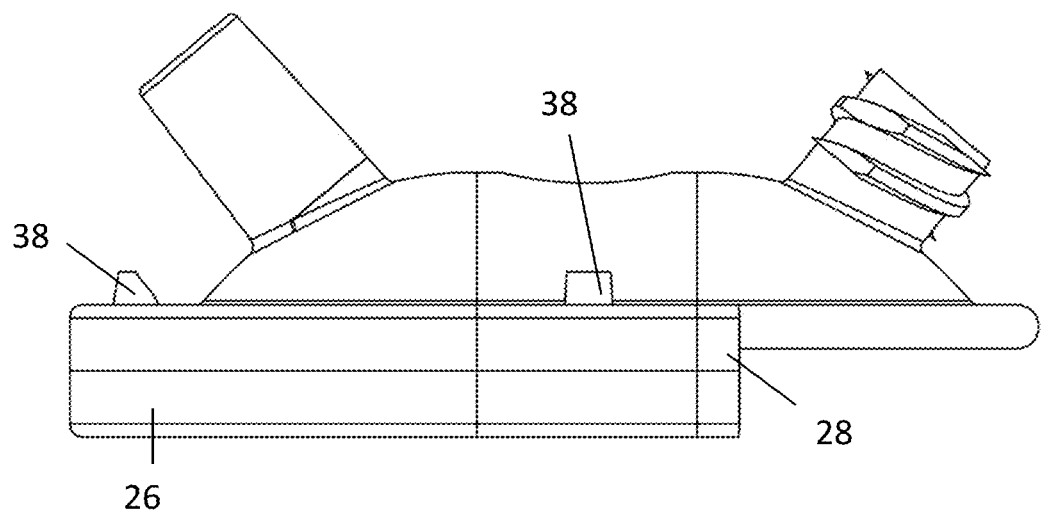

FIGS. 16-18 show another embodiment of the adaptor 1 with a collar 26. In this embodiment, clips 34 on the collar 26 are secured by slots 36 on a partial extended rail 28 of the adaptor 1. FIG. 18 shows the head 38 of the clip extending through the slot and snap together such that the collar 26 and the adaptor 1 are locked together.

Figure 19:
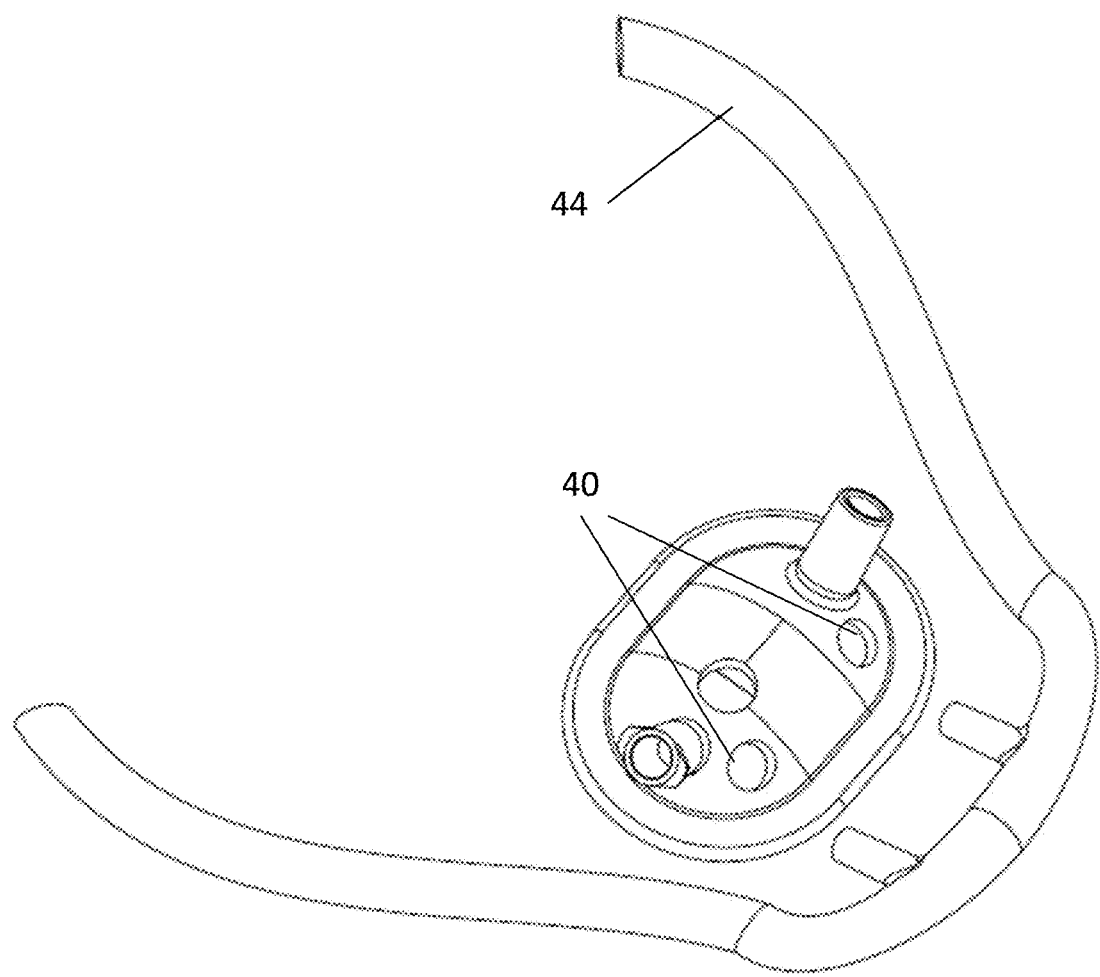
FIGS. 19-20 illustrate a sixth embodiment of the adaptor.
Figure 20:
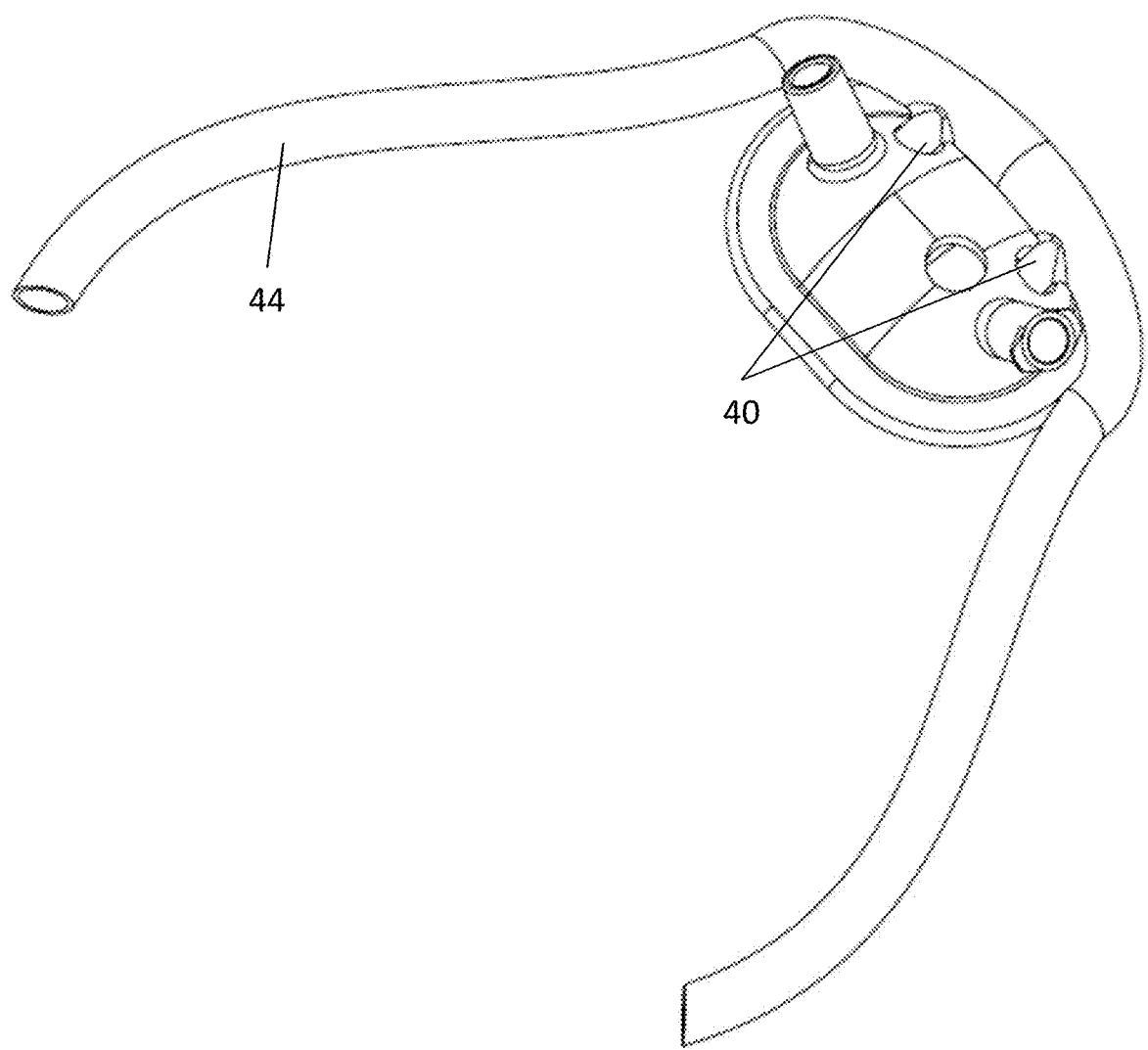

FIGS. 19-20 shows a sixth embodiment of the adaptor 1. The body has a pair of openings 40 that receives the prongs 42 of a nasal cannula 44. Typically, the prongs 42 are positioned in the nostrils of a patient to provide supplemental oxygen or air flow. FIG. 19 shows the adaptor 1 and the nasal cannula separated from each other. FIG. 20 shows the prongs 42 of the nasal cannula 44 inserted in the adaptor.

Figure 21:
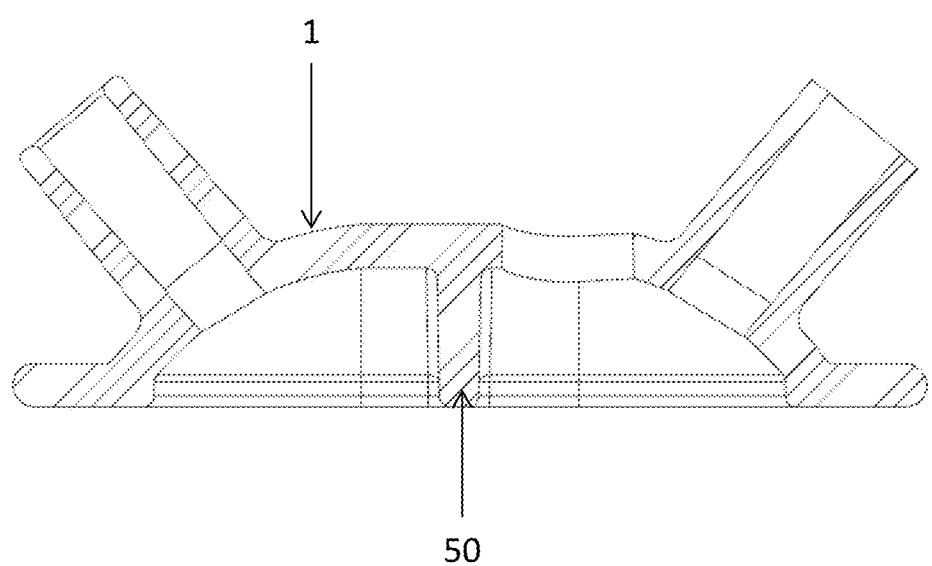
FIG. 21 illustrates a cross-sectional view of a seventh embodiment of the adaptor.

FIG. 21 shows a cross-sectional view of another embodiment of the adaptor 1 with a septum 50 that divides the inner dome volume into two equal sections to improve CO2 capture.

Figure 22:
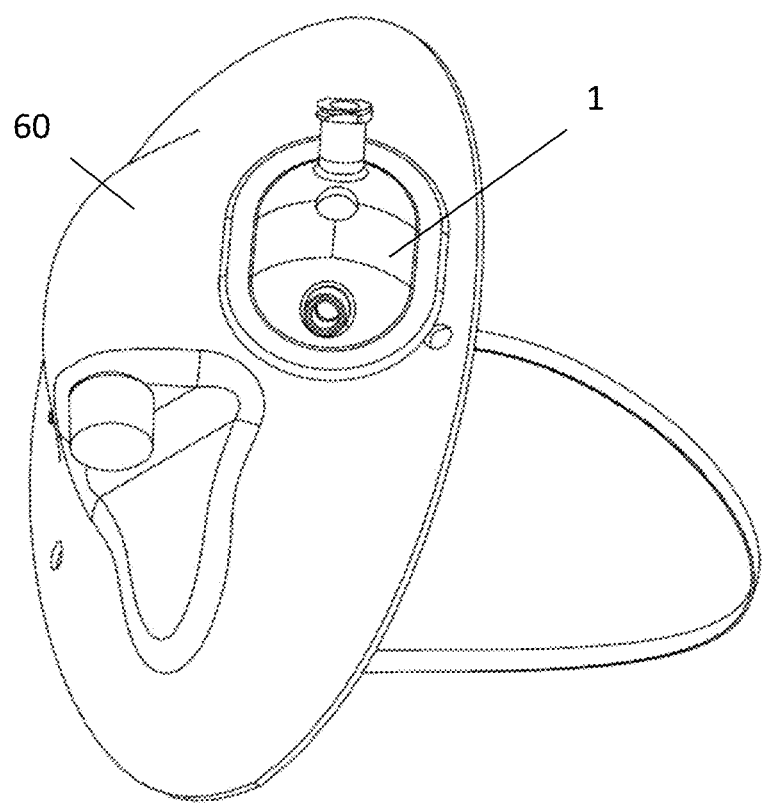
FIG. 22 illustrates an adaptor attached to an oxygen mask.

FIG. 22 shows an adaptor 1 attached to an oxygen mask 60.

The CDAA may be applied prior to OPA insertion or once the airway is already in place. The same applies to facemask application. Simply remove the adhesive backing, and attach the CDAA to that part of the OPA that protrudes above the patient's mouth. Connect the end-tidal CO2 sampling tubing to the Luer Lock port of the CDAA. A secondary port is available for supplemental oxygen delivery.

In a similar fashion the adaptor is placed over the perforations on the side of the facemask. Supplemental oxygen is already provided in this situation. In addition a suction/ventilation opening is located on the top of the adaptor.

The CDAA is designed to fit a wide range of OPA and facemask sizes as well as many different brands currently being used. It is designed for single use. The CDAA is low cost, safe and easy to apply.

While the present invention is described herein with reference to particular applications, the invention is not limited to these applications. Those of ordinary skill in the art and access to the teachings provided herein will recognize additional modifications, applications, and embodiments within the scope hereof and additional fields in which the present invention could be utilized. For example, small tubes (not shown) may be attached to each docking channel inside the dome-shaped body 10. These tubes may be used to ensure separation of oxygen supplementation from $CO_2$ monitoring. Therefore, the claims recited below cover any and all such applications, modifications and embodiments within the scope of the present invention.

The invention claimed is:

1. An airway adaptor, comprising:
   a dome-shaped body;
   an attachment mechanism at a peripheral edge of the dome-shaped body that is removably attachable directly to a flange of an oropharyngeal airway device and removably attachable directly to an oxygen facemask; and
   a pair of circular openings in the dome-shaped body for receiving nostril prongs of a nasal cannula.

2. The airway adaptor of claim 1, wherein the attachment mechanism comprises a pair of clips.

3. The airway adaptor of claim 1, wherein the attachment mechanism comprises four clips.

4. The airway adaptor of claim 1, wherein the attachment mechanism comprises a rail around a portion of the dome-shaped body.

5. The airway adaptor of claim 1, wherein the attachment mechanism comprises a pair of brackets around a portion of the dome-shaped body.

6. The airway adaptor of claim 1, wherein the attachment mechanism comprises a continuous ridge around the dome-shaped body.

7. The airway adaptor of claim 6, wherein the attachment mechanism comprises a rail extending from a portion of the continuous ridge.

8. The airway adaptor of claim 6, further comprising:
a collar that attaches to the continuous ridge to fix the oropharyngeal airway device between the collar and the continuous ridge.

9. The airway adaptor of claim 6, further comprising:
a ring with an adhesive on a front surface and a back surface,
wherein the front surface attaches to the continuous ridge and the back surface attaches to the oropharyngeal airway device.

10. The airway adaptor of claim 1, further comprising:
a port in the dome-shaped body to provide an airway and access for suctioning;
a first docking sleeve in the dome-shaped body to provide oxygen supplementation; and
a second docking sleeve in the dome-shaped body to provide end-tidal CO2 monitoring.

11. An oropharyngeal adaptor, comprising:
a dome-shaped body;
a flat ridge at a peripheral edge of the dome-shaped body that is removably attachable directly to a flange of an oropharyngeal airway device and removably attachable directly to an oxygen facemask;
a first port in the dome-shaped body to provide an airway and access for suctioning;
a second port in the dome-shaped body to provide oxygen supplementation;
a third port in the dome-shaped body to provide end-tidal CO2 monitoring; and
a pair of circular openings in the dome-shaped body for receiving nostril prongs of a nasal cannula.

12. The oropharyngeal adaptor of claim 11, further comprising:
a collar with clips; and
slots in the flat ridge to receive the clips,
wherein the flange of the oropharyngeal airway device is fixed between the flat ridge and the collar.

13. The oropharyngeal adaptor of claim 11, further comprising a rail extending from a portion of the flat ridge.

14. The oropharyngeal adaptor of claim 13, further comprising:
a collar with clips that protrude away from the collar; and
slots in the rail to receive the clips,
wherein the flange of the oropharyngeal airway device is fixed between the collar and the rail.

15. The oropharyngeal adaptor of claim 13, further comprising:
a collar with brackets that protrude away from the collar,
wherein the flange of the oropharyngeal airway device is fixed between the collar and the rail by attaching the brackets to the rail.

16. The oropharyngeal adaptor of claim 15, wherein the rail includes slots to receive the brackets.

17. The oropharyngeal adaptor of claim 11, further comprising:
a ring with an adhesive on a front surface and a back surface,
wherein the front surface attaches to the flat ridge and the back surface attaches to the oropharyngeal airway device.

18. An oropharyngeal adaptor system comprising:
an oropharyngeal airway device that provides an airway for a patient;
an oropharyngeal adaptor that includes:
a body,
a pair of circular openings in the body, and
an attachment mechanism at a peripheral edge of the body that is removably attachable directly to a flange of the oropharyngeal airway device and removably attachable directly to an oxygen facemask; and
a nasal cannula with nostril prongs that are received in the pair of circular openings of the adaptor.

19. The oropharyngeal adaptor system of claim 18, wherein the oropharyngeal adaptor further comprises:
a port in the body to provide an airway and access for suctioning;
a first docking sleeve in the body to provide oxygen supplementation; and
a second docking sleeve in the body to provide end-tidal CO2 monitoring.

20. The oropharyngeal adaptor system of claim 18, wherein the attachment mechanism of the oropharyngeal adaptor comprises clips, brackets, a rail, a ridge, or a ring.

* * * * *